United States Patent [19]
Caubere et al.

[11] Patent Number: 6,127,369

[45] Date of Patent: Oct. 3, 2000

[54] 5,10-DIHYDRODIPYRIDO[2,3-B:2,3-E] PYRAZIN AND 5,10-DIHYDRODIPYRIDO[2,3-B:3,2-E]PYRAZIN COMPOUNDS

[75] Inventors: Paul Caubere, Saint-Vincent; Gérald Guillaumet, Saint-Jean-le-Blanc; Ivan Rodriguez, Cauffry; Karine Vinter-Pasquier, Thaon-les-Vosges; Catherine Kuehm-Caubere, Courbevoie; Stéphanie Blanchard, Olivet; Ghanem Atassi, Saint Cloud; Alain Pierre, Les-Alluets-le-Roi; Bruno Pfeiffer, Saint-Leu-la-Foret; Pierre Renard, Le Chesnay, all of France

[73] Assignee: Adir et Compagnie, Courbevoie, France

[21] Appl. No.: 09/330,496

[22] Filed: Jun. 11, 1999

[30] Foreign Application Priority Data

Jun. 12, 1998 [FR] France .................................. 98 07447

[51] Int. Cl.[7] ...................... A61K 31/4985; A61P 35/02; A61P 35/00; C07D 471/14
[52] U.S. Cl. ......................... 514/250; 544/225; 544/229; 544/345
[58] Field of Search .............................. 544/345; 514/250

[56] References Cited

PUBLICATIONS

Rodriguez, I. et al. Design of New Anticancer Drugs. I. Easy Hetarynic Access to Dihydrodipyridopyrazines, a New Family of Antitumor Agents. Tetrahedron Letters 39 (1998), 7283–7286.

*Primary Examiner*—Michael G. Ambrose
*Attorney, Agent, or Firm*—The Firm of Gordon W. Hueschen

[57] ABSTRACT

A compound selected from those of formula (I):

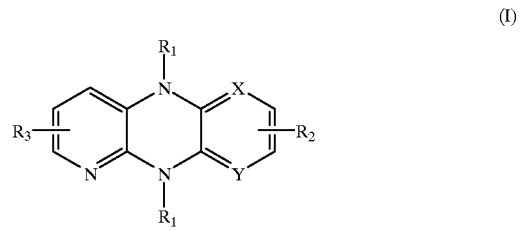

wherein:

X represents N, C or CH,

Y represents N when X represents C or CH, or Y represents C or CH when X represents N, $R_1$ represents an optionally substituted alkyl, $R_2$ and $R_3$, which may be identical or different, represent Z or W, as defined in the description, their isomers and addition salts thereof with a pharmaceutically-acceptable acid or base, and medicinal products containing the same which are useful in the treatment of cancer.

16 Claims, No Drawings

5,10-DIHYDRODIPYRIDO[2,3-B:2,3-E] PYRAZIN AND 5,10-DIHYDRODIPYRIDO[2,3-B:3,2-E]PYRAZIN COMPOUNDS

FIELD OF THE INVENTION

The present invention relates to new 5,10-dihydrodipyrido-[2,3-b:2,3-e]- and -[2,3-b:3,2-e]-pyrazin compounds. The compounds of the invention, in addition to bring new, surprisingly have a valuable in vitro and in vivo activity for that type of compound. The new compounds discovered by the Applicant accordingly have anti-tumour properties which make then especially suitable for use in the treatment of cancers.

DETAILED DESCRIPTION OF THE INVENTION

More specifically, the present invention relates to compounds of formula (I):

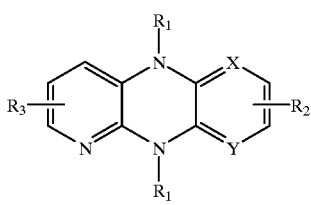

(I)

wherein:

X represents a nitrogen atom, a carbon atom or a CH group,

Y represents a nitrogen atom when X represents a carbon atom or a CH group, or Y represents a carbon atom or a CH group when X represents a nitrogen atom, it being understood that when X or Y represents a carbon atom then this carbon atom is substituted by the $R_2$ group, $R_1$ represents a linear or branched ($C_1$–$C_6$)alkyl group (optionally substituted by one or more identical or different groups selected from halogen atom, linear or branched ($C_1$–$C_6$)-alkylthio, linear or branched ($C_1$–$C_6$)alkoxy, monoalkyl- or dialkyl-amino wherein alkyl in each case is linear or branched and has from 1 to 6 carbon atoms, aryl, hydroxy, formyl, linear or branched ($C_1$–$C_6$)alkoxycarbonyl, and carboxy), it being understood that the two $R_1$ groups have either identical group definitions or different group definitions, $R_2$ and $R_3$, which may be identical or different, each independently of the other represent a Z group, or one of the groups $R_2$ and $R_3$ represents a W group and the other of the groups $R_2$ and $R_3$ represents a Z group, in which Z and W groups:

—Z represents:

a hydrogen atom, a halogen atom a linear or branched ($C_1$–$C_6$)alkyl group, which alkyl group may be substituted by one or more identical or different groups selected from hydroxy, linear or branched ($C_1$–$C_6$)alkoxy, aryl, amino (optionally substituted by one or two identical or different groups selected from linear or branched ($C_1$–$C_6$) alkyl, aryl, aryl-($C_1$–$C_6$)alkyl in which the alkyl moiety is linear or branched, aminoalkyl in which alkyl is linear or branched and has from 1 to 6 carbon atoms, monoalkylaminoalkyl in which each alkyl is linear or branched and has from 1 to 6 carbon atoms, dialkylaminoalkyl in which each alkyl is linear or branched and has from 1 to 6 carbon atoms, linear or branched ($C_1$–$C_6$)-hydroxyalkyl, and alkoxyalkyl in which each alkyl moiety is linear or branched and has from 1 to 6 carbon atoms) and formyl, amino (optionally substituted by one or two identical or different groups selected from linear or branched ($C_1$–$C_6$)alkyl, aryl, aryl-($C_1$–$C_6$)alkyl in which the alkyl moiety is linear or branched, linear or branched ($C_1$–$C_6$)-alkylsulphonyl, arylsulphonyl, aminoalkyl in which alkyl is linear or branched and has from 1 to 6 carbon atoms, monoalkylaminoalkyl in which each alkyl is linear or branched and has from 1 to 6 carbon atoms, dialkylaminoalkyl in which each alkyl is linear or branched and has from 1 to 6 carbon atoms, linear or branched ($C_1$–$C_6$)-hydroxyalkyl, and alkoxyalkyl in which each alkyl moiety is linear or branched and has from 1 to 6 carbon atoms), nitro, linear or branched ($C_1$–$C_6$)alkylthio, formyl, hydroxycarbonyl, linear or branched ($C_1$–$C_6$)alkoxycarbonyl group, aminocarbonyl, monoalkylaminocarbonyl in which alkyl is linear or branched and has from 1 to 6 carbon atoms, or a dialkylaminocarbonyl group in which each alkyl is linear or branched and has from 1 to 6 carbon atoms, W represents a linear or branched ($C_5$–$C_{24}$)alkylene chain, in which one or more carbon atoms are optionally replaced by one or more identical or different groups each independently of the other selected from oxygen atoms, imine groups, —N($R_4$)—CO—, —CO—N($R_4$)—, and N($R_4$) groups wherein $R_4$ represents a hydrogen atom, a linear or branched ($C_1$–$C_6$) alkyl group, an aryl group, or an aryl-($C_1$–$C_6$)alkyl group in which the alkyl moiety is linear or branched, which alkylene chain is substituted in its terminal position by any one of the following groups:

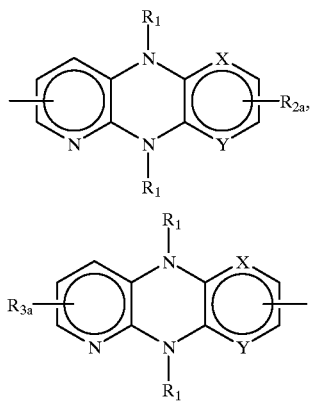

wherein X, Y and $R_1$ are as defined above, and $R_{2a}$ and $R_{3a}$ represent a Z group as defined above, their isomers and addition salts thereof with a pharmaceutically acceptable acid or base.

Among the pharmaceutically acceptable acids there may be mentioned by way of non-limiting example hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid, etc.

Among the pharmaceutically acceptable bases there may be mentioned by way of non-limiting example sodium hydroxide, potassium hydroxide, triethylamine, tert-butylamine, etc.

The term "aryl group" is understood to mean a phenyl, naphthyl, tetrahydronaphthyl, dihydronapththyl, indenyl or indanyl group, each of those groups optionally being substituted by one or more identical or different substituents selected from halogen atoms, hydroxy groups, cyano groups, nitro groups, linear or branched ($C_1$–$C_6$)alkyl groups, linear or branched trihalo-$C_1$–$C_6$)alkyl groups, linear or branched ($C_1$–$C_6$)alkoxy groups, linear or branched ($C_1$–$C_6$)acyl groups, carboxy groups, linear or branched ($C_1$–$C_6$)-alkoxycarbonyl groups, and amino groups (amino optionally being substituted by one or two identical or different groups selected from linear or branched ($C_1$–$C_6$) alkyl, aryl, and aryl-($C_1$–$C_6$)alkyl in which the alkyl moiety is linear or branched).

According to an advantageous embodiment of the invention, the preferred compounds are those wherein $R_2$ and $R_3$, which may be identical or different, each independently of the other represent a Z group.

According to another advantageous embodiment, the preferred compounds of the invention are those wherein one of the groups $R_2$ and $R_3$ represents a Z group and the other of the groups $R_2$ and $R_3$ represents a W group.

According to an especially preferred embodiment, the preferred compounds of the invention are those wherein one of the groups $R_2$ and $R_3$ represents a Z group and the other of the groups $R_2$ and $R_3$ represents a $W_1$ group, which $W_1$ group represents a linear ($C_6$–$C_{12}$)-alkylene chain in which two or three carbon atoms are replaced by two or three identical or different N($R_4$) groups wherein $R_4$, which may be identical or different, represents a hydrogen atom or a linear or branched ($C_1$–$C_6$)alkyl group, which alkylene chain is substituted in its terminal position by any one of the following two groups:

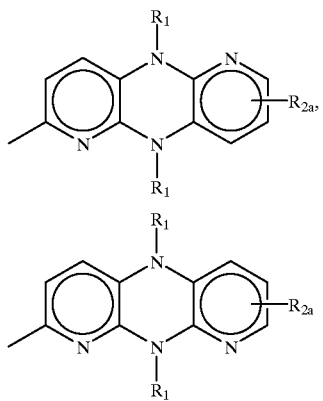

wherein $R_1$ is as defined for the general formula (I) and $R_{2a}$ represents a Z group.

According to another preferred embodiment, the preferred compounds of the invention are those wherein one of the groups $R_2$ and $R_3$ represents a Z group and the other of the groups $R_2$ and $R_3$ represents a $W_2$ group with a formula:

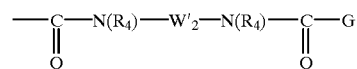

wherein:

$R_4$, which may be identical or different, represents a hydrogen atom or a linear or branched ($C_1$–$C_6$)alkyl group, $W'_2$ represents a linear ($C_3$–$C_{12}$)-alkylene chain in which one, two or three carbon atoms are eventually replaced by one, two or three identical or different N($R_4$)groups wherein $R_4$ is as defined above, G represents any one of the following groups:

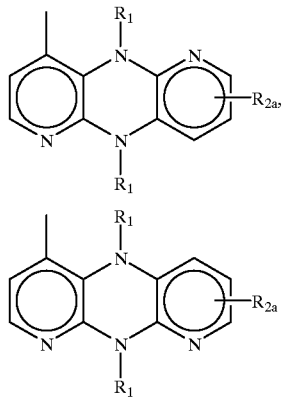

wherein $R_1$ is as defined for formula (I) and $R_{2a}$ represents a Z group.

According to preferred embodiment, the preferred compounds of the invention are those wherein one of the groups $R_2$ and $R_3$ represents a $W_1$ group or $W_2$ group, each being as defined above, and wherein $R_1$ groups represent a linear or branched ($C_1$–$C_6$) alkyl group and $R_{2a}$ represents a hydrogen atom, and the other of the groups $R_2$ and $R_3$ represents a Z group corresponding to a hydrogen atom.

The preferred $R_1$ substituent according to the invention is the linear or branched ($C_1$–$C_6$)-alkyl group.

In an especially valuable embodiment, the preferred compounds of the invention are:

—N1,N2-di[(5,10-dimethyl-5,10-dihydrodipyrido[2,3-b:3,2-e]pyrazin-2-yl)methyl]-1,2-ethanediamine, —N1,N3-di[(5,10-dimethyl-5,10-dihydrodipyrido[2,3-b:3,2-e]pyrazin-2-yl)methyl]-1,3-propanediamine, —N1,N4-di[(5,10-dimethyl)-5,10-dihydrodipyrido-[2,3-b:3,2-]pyrazin-2-yl)methyl]-1,4-butanediamine, —N1-[(5,10-dimethyl-5,10-dihydrodipyrido-[2,3-b:3,2-e]pyrazin-2-yl)methyl]-N3-(3-{[5,10-dimethyl-5,10-dihydrodipyrido[2,3-b:3,2-e]pyrazin-2-yl)methyl]amino}propyl)-N3-methyl-1,3-propanediamine, and —N1,N7-di[(5,10-dimethyl-5,10-dihydrodipyrido-[2,3-b:3,2-e]pyrazin-2-yl)methyl]-1,7-heptanediamine.

The isomers and addition salts with a pharmaceutically acceptable acid or base of the preferred compounds form an integral part of the invention.

The invention relates also to a process for the preparation of the compounds of formula (I), characterised in that there is used as starting material a 3-halo-2-amino-pyridine of formula (II):

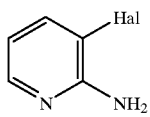 (II)

wherein Hal represents a halogen atom, which compounds of formula (II) are reacted under basic conditions with a compound of formula (III):

 (III)

wherein Hal represents a halogen atom and $R'_1$ represents a linear or branched $(C_1-C_6)$alkyl group, optionally substituted by a linear or branched $(C_1-C_6)$alkoxy group, a monoalkyl- or dialkyl-amino group wherein alkyl in each case is linear or branched and has from 1 to 6 carbon atoms, or by an aryl group, to yield the compounds of formula (IV):

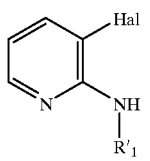 (IV)

wherein Hal and $R'_1$ are as defined above, which compound of formula (IV) is condensed with itself in the presence of a complex base, to yield the compounds of formula (I/a), a particular case of the compounds of formula (I):

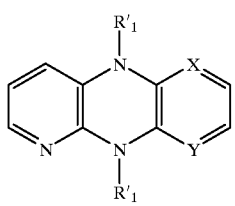 (I/a)

wherein $R'_1$ is as defined above and X and Y are as defined for formula (I), which compounds of formula (I/a), in the particular case where $R'_1$ represents an $R''_1$ group consisting of a linear $(C_1-C_6)$alkyl group, are subjected, if desired, to a metallation reaction and the intermediate anion of which is trapped by a dialkylsulphidealkyl halide in which each alkyl is linear or branched and has from 1 to 6 carbon atoms, an alkoxyalkyl halide in which each alkyl is linear or branched and has from 1 to 6 carbon atoms, a halide, an aldehyde, a ketone, a carboxyl compound, or an alkoxycarbonyl compound in which the alkyl is linear or branched and has from 1 to 6 carbon atoms, to yield the compounds of formulae (I/b) and (I/b'), and/or (I/c), the products (I/b') being coproducts of reaction:

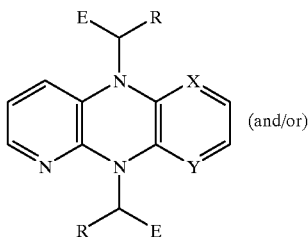 (I/b)

(and/or)

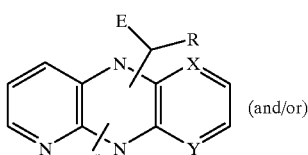 (I/b')

(and/or)

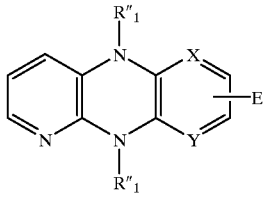 (I/c)

wherein X, Y and $R''_1$ are as defined above, R represents a hydrogen atom or a linear $(C_1-C_5)$alkyl group and E represents a halogen atom, a linear or branched $(C_1-C_6)$alkyl group, a linear or branched $(C_1-C_6)$alkylthio group, a formyl group, a linear or branched $(C_1-C_6)$alkyl group substituted by a linear or branched $(C_1-C_6)$alkoxy group, or a linear or branched $(C_1-C_6)$-alkyl group substituted by one or more identical or different groups selected from aryl, hydroxy, formyl, linear or branched $(C_1-C_6)$alkoxycarbonyl, and carboxy, the totality of the compounds of formulae (I/a), (I/b) and (I/b') constituting the compounds of formula (I/d):

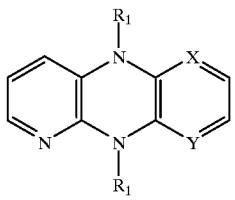 (I/d)

wherein $R_1$, X and Y are as defined for formula (I), which compounds of formula (I/d), are treated, if desired, with a nitrating agent, to yield the compounds of formula (I/e), a particular case of the compounds of formula (I), (I/e)

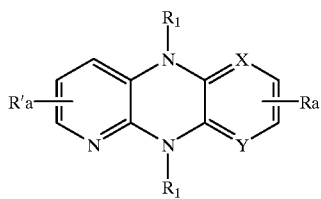

wherein X, Y and R₁ are as defined above,
and Ra and R'a, which may be identical or different, represent a hydrogen atom or a nitro group, it being understood that Ra and R'a cannot simultaneously represent a hydrogen atom,
the nitro function(s) of which compounds of formula (I/e) is/are, if desired, reduced to the amine function, to yield the compounds of formula (I/f), a particular case of the compounds of formula (I):

(I/f)

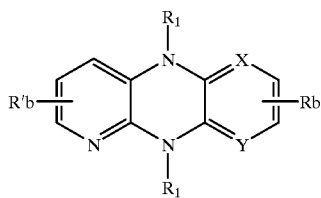

wherein X, Y and R₁ are as defined above and Rb and R'b, which may be identical or different, represent a hydrogen atom or an amino group, it being understood that Rb and R'b cannot simultaneously represent a hydrogen atom,
which compounds of formula (I/f) are treated under basic conditions with an electrophilic compound, to yield the compounds of formula (I/g), a particular case of the compounds of formula (I):

(I/g)

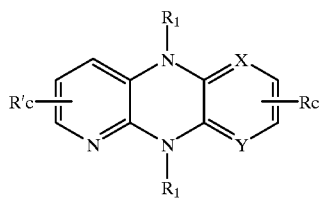

wherein X, Y and R₁ are as defined above, and Rc and R'c, which may be identical or different, represent a hydrogen atom or an amino group substituted by one or two identical or different groups selected from linear or branched ($C_1$–$C_6$) alkyl, aryl, aryl-($C_1$–$C_6$)alkyl in which the alkyl moiety is linear or branched, linear or branched ($C_1$–$C_6$) alkylsulphonyl, arylsulphonyl, aminoalkyl in which alkyl is linear or branched and has from 1 to 6 carbon atoms, monoalkylaminoalkyl in which each alkyl is linear or branched and has from 1 to 6 carbon atoms, dialkylaminoalkyl in which each alkyl is linear or branched and has from 1 to 6 carbon atoms, linear or branched ($C_1$–$C_6$)-hydroxyalkyl, and alkoxyalkyl in which each alkyl moiety is linear or branched and has from 1 to 6 carbon atoms, it being understood that Rc and R'c cannot simultaneously represent a hydrogen atom,
or which compounds of formula (I/d) are subjected to conditions of a formylation reaction, to yield the compounds of formula (I/h), a particular case of the compounds of formula (I):

(I/h)

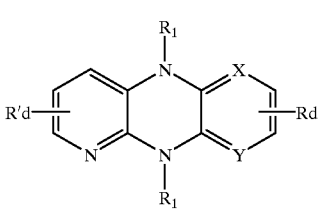

wherein X, Y and R₁ are as defined above and Rd and R'd, which may be identical or different, represent a formyl group or a hydrogen atom, it being understood that Rd and R'd cannot simultaneously represent a hydrogen atom,
which compounds of formula (I/h)
are treated with an oxidising agent and then are eventually subjected to the action of an alcohol, to yield the compounds of formula (I/h'), a particular case of the compounds of formula (I):

(I/h')

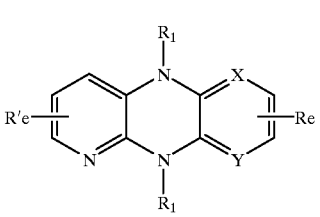

wherein R₁, X and Y are as defined above and Re and R'e, which may be identical or different, represent a hydrogen atom, a hydroxycarbonyl group or a linear or branched ($C_1$–$C_6$)alkoxycarbonyl group, it being understood that R'e and Re cannot simultaneously represent a hydrogen atom, compounds of formula (I/h') wherein at least one of the Re or R'e groups are eventually changed into acid chloride according to conventional conditions of organic synthesis, or compounds of formula (I/h') react directly with an amino compound, under peptidic coupling conditions, to yield the compounds of formula (I/h'₁), a particular case of the compounds of formula (I):

(I/h'₁)

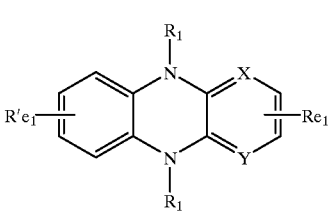

wherein R₁, X and Y are as defined above, and Re₁ and R'e₁, which may be identical or different, represent a hydrogen atom, an aminocarbonyl, a monoalkylaminocarbonyl in which alkyl is linear or branched and has from 1 to 6 carbon atoms, or a dialkylaminocarbonyl group in which each alkyl is linear or branched and has from 1 to 6 carbon atoms, it being understood that Re₁ and R'e₁ cannot simultaneously represent a hydrogen atom,
or are subjected to conditions of reductive amination to yield the compounds of formula (I/i), a particular case of the compounds of formula (I):

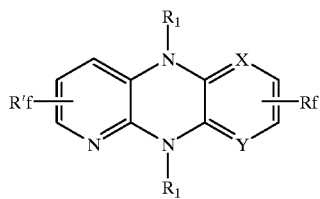
(I/i)

wherein X, Y and $R_1$ are as defined above and Rf and R'f, which may be identical or different, represent a hydrogen atom or a group of formula $CH_2-NR_{10}-R_{20}$ wherein $R_{10}$ and $R_{20}$, which may be identical or different, represent a hydrogen atom, a linear or branched ($C_1-C_6$)alkyl group, an aryl group, an aryl-($C_1-C_6$)alkyl group in which the alkyl moiety is linear or branched, an aminoalkyl group in which alkyl is linear or branched and has from 1 to 6 carbon atoms, a monoalkylaminoalkyl group in which each alkyl is linear or branched and has from 1 to 6 carbon atoms, a dialkylaminoalkyl group in which each alkyl is linear or branched and has from 1 to 6 carbon atoms, a linear or branched ($C_1-C_6$)-hydroxyalkyl group, or an alkoxyalkyl group in which each alkyl moiety is linear or branched and has from 1 to 6 carbon atoms, it being understood that Rf and R'f cannot simultaneously represent a hydrogen atom, or are treated with a phosphorus ylid prepared starting from a compound of formula (V):

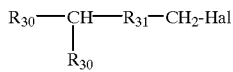
(V)

wherein Hal represents a halogen atom, $R_{31}$ represents a linear or branched ($C_1-C_4$)alkylene chain, and $R_{30}$ represents an aldehyde-protecting group, such as an acetal, to yield the compounds of formula (VI):

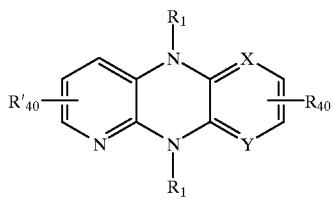
(VI)

wherein X, Y and $R_1$ are as defined and $R_{40}$ and $R'_{40}$ represent a hydrogen atom or a group of formula:

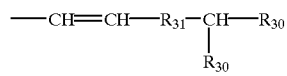

wherein $R_{31}$ and $R_{30}$ are as defined above, the double bond of which compounds of formula (VI) is reduced according to conventional conditions of organic synthesis, and the terminal aldehyde function of which is then deprotected, to yield the compounds of formula (I/j), a particular case of the compounds of formula (I):

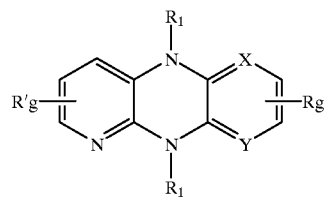
(I/j)

wherein X, Y and $R_1$ are as defined above and Rg and R'g, which may be identical or different, represent a hydrogen atom or a linear or branched ($C_1-C_6$)alkyl group, substituted by a formyl group, it being understood that Rg and R'g cannot simultaneously represent a hydrogen atom, which compounds of formula (I/j) are subjected to conditions of reductive amination to yield the compounds of formula (I/k), a particular case of the compounds of formula (I):

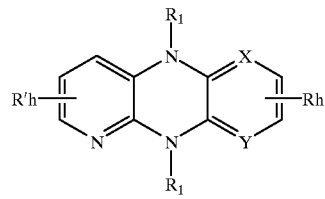
(I/k)

wherein X, Y and $R_1$ are as defined above and Rh and R'h, which may be identical or different, represent a hydrogen atom or a linear or branched ($C_1-C_6$)alkyl group, substituted by a group of formula $CH_2-NR_{10}R_{20}$ wherein $R_{10}$ and $R_{20}$ are as defined above, it being understood that Rh and R'h cannot simultaneously represent a hydrogen atom, or which compounds of formula (I/d) are subjected to the action of a halogenating agent, such as, for example, phenyltrimethylammonium tribromide, to yield the compounds of formula (I/l), a particular case of the compounds of formula (I):

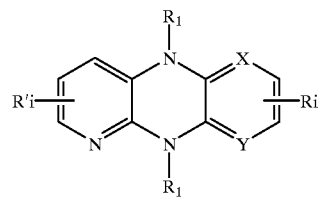
(I/l)

wherein X, Y and $R_1$ are as defined above and Ri and R'i, which may be identical or different, represent a hydrogen atom or a halogen atom, it being understood that Ri and R'i do not simultaneously represent a hydrogen atom, it being understood that the reactions described above, carried out starting from the compounds of formula (I/d), enable there to be obtained one or more products substituted on one pyridinyl ring or on the other pyridinyl ring, or on both pyridinyl rings, that those various reactions may be carried out in any order starting from the compounds of formula (I/d) and/or (I/c), and that, by judicious selection on the part of the person skilled in the art, in terms of the reagents used, the order in which the reactions are carried out, and the reaction conditions, it is thus possible to obtain, starting from the compounds of formulae (I/d) and (I/c), any one of the compounds of formula (I/m), a particular case of the compounds of formula (I):

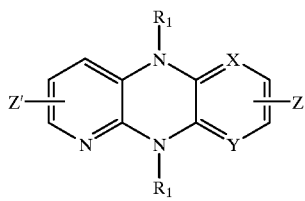

(I/m)

wherein X, Y, $R_1$ and Z are as defined for formula (I), and Z' represents any of the definitions of Z, which compounds of formula (I/m) are treated, if desired, either, when one of the groups Z and Z' represents an amino group or an aminoalkyl group in which alkyl is linear or branched and has from 1 to 7 carbon atoms, under conditions of amination or reductive amination, with a compound of formula (VII):

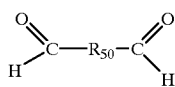

(VII)

wherein $R_{50}$ represents a linear or branched alkylene chain, wherein one or more carbon atoms are optionally replaced by one or more groups selected from oxygen atoms and $N(R_4)$ groups wherein $R_4$ is as defined for formula (I), or with a compound of formula (VIII):

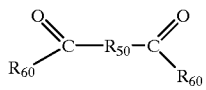

(VIII)

wherein $R_{60}$ represents a chlorine atom or a linear or branched $(C_1-C_6)$alkoxy group, and $R_{50}$ is as defined above, or, when one of the groups Z and Z' represents a formyl group or a linear or branched formyl-$(C_1-C_6)$alkyl group, with a compound of formula (IX), under conditions of amination or reductive amination:

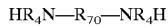

(IX)

wherein $R_4$ is as defined for formula (I) and $R_{70}$ represents a linear or branched alkylene chain wherein one or more carbon atoms may optionally be replaced by one or more groups selected from oxygen atoms and $NR_4$ groups wherein $R_4$ is as defined above, or, when one of the groups Z and Z' represents a linear or branched $(C_1-C_6)$ alkoxycarbonyl group, or an acid chloride, with a compound of formula (IX) as defined above, under conventional conditions of peptidic coupling, to yield the compounds of formula (I/n) or (I/o), a particular case of the compounds of formula (I):

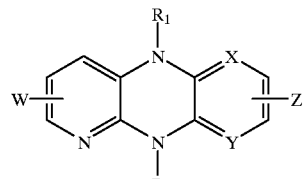

(I/n)

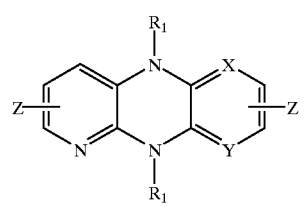

(I/o)

wherein X, Y, $R_1$, Z and W are as defined for formula (I), and Z' is as defined above, it being understood that the groups $R_{50}$ and $R_{70}$ defined above, have a length of the chain as it permit to obtain the compounds (I/n) and (I/o) in which W group has from 5 to 24 chain members, which compounds (I/a) to (I/o) constitute the totality of the compounds of the invention, which are purified, if necessary, according to a conventional purification technique, which may, if desired, be separated into their different isomers according to a conventional separation technique, and which are converted, where appropriate, into addition salts thereof with a pharmaceutically acceptable acid or base.

According to a variation for obtaining the compounds of the invention, the compounds of formula (I/a) may, if desired, be subjected to a metallation reaction in which the intermediate anion is trapped by a tin, boron or silicon compound, enabling the compounds of formulae (α) and (β), and/or (χ) to be obtained:

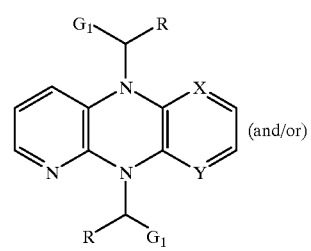

α

(and/or)

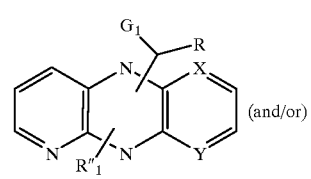

β

(and/or)

-continued

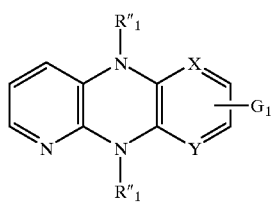

wherein:
X and Y are as defined for formula (I),
R"$_1$ represents a linear ($C_1$–$C_6$)alkyl group,
R represents a hydrogen atom or a linear ($C_1$–$C_5$)alkyl group, and $G_1$ represents a tin, boron or silicon atom, each of those atoms being substituted by one or more linear or branched ($C_1$–$C_6$)alkyl groups.

Those compounds of formulae (α), (β) and (χ) are useful as synthesis intermediates for obtaining the compounds of formula (I).

In fact, these compounds may be treated under coupling reaction condition catalyzed by Palladium, to introduce an alkyl lateral side-chain optionally substituted. By judicious selection of the coupling reagent, it is then possible to obtain from those intermediates, and more particularly from intermediate of formula (χ), the compounds of formula (I) wherein one of the groups $R_2$ and $R_3$ represents a Z group with Z being a linear or branched ($C_1$–$C_6$)-alkyl group optionally substituted by one or more groups as defined in formula (I).

The compounds of formulae (II), (III), (V), (VII), (VIII) and (IX) are either commercial compounds, or are obtained according to conventional methods of organic synthesis.

The compounds of formula (I) have especially valuable anti-tumour properties. They have excellent in vitro cytotoxicity on cell lines, and an activity in respect of the cell cycle. The characteristic properties of the compounds enable them to be used therapeutically as anti-tumour agents.

The present invention relates also to pharmaceutical compositions comprising as active ingredient at least one compound of formula (I), an optical isomer thereof or an addition salt thereof with a pharmaceutically acceptable acid or base, on its own or in combination with one or more inert, non-toxic pharmaceutically acceptable excipients or carriers.

Among the pharmaceutical compositions according to the invention, there may be mentioned more especially those that are suitable for oral, parenteral (intravenous, intramuscular or sub-cutaneous), per- or trans-cutaneous, nasal, rectal, perlingual, ocular or respiratory administration, and especially tablets or dragées, sublingual tablets, sachets, gelatin capsules, lozenges, suppositories, creams, ointments, dermal gels, injectable or drinkable preparations, aerosols, eye or nose drops, etc.

The useful dosage varies according to the age and weight of the patient, the route of administration, the nature and severity of the disorder and whether any associated treatments are being taken, and ranges from 1 mg to 250 mg in one or more administrations per day.

The following Examples illustrate the invention but do not limit it in any way. The starting materials used are known products or are prepared according to known procedures.

The various preparations yield synthesis intermediates for use in the preparation of the compounds of the invention.

The structures of the compounds described in the Examples and in the Preparations were determined according to the usual spectrophotometric techniques (infrared, nuclear magnetic resonance, mass spectrometry).

Preparation A

2-Amino-3-bromopyridine

Step A:N1-(2-Pyridyl)-2,2-dimethylpropanamide 1.1 equivalents of pivalic acid chloride dissolved in 100 ml of dichloromethane are added dropwise at 0° C. to a solution containing one equivalent of 2-aminopyridine and 1.25 equivalents of triethylamine in 400 ml of dichloromethane. Once the addition is complete, the reaction mixture is brought to room temperature for three hours, and then the reaction mixture is washed with a saturated NaHCO$_3$ solution. After drying of the organic phase, filtration and concentration under reduced pressure, the resulting residue is crystallised from hexane, enabling the expected product to be isolated by filtration.

Step B:N1-(3-Bromo-2-pyridyl)-2,2-dimethylpropanamide

One equivalent of the product obtained in Step A is added dropwise to a solution, at −30° C., of 2.5 equivalents of 1.6M n-butyllithium dissolved in hexane. Once the addition is complete, the reaction mixture is brought back to 0° C. After four hours' reaction, the solution is cooled to −78° C. and 3 equivalents of dibromo-1,2-ethane are added rapidly. The reaction mixture is then brought slowly back to room temperature and is then hydrolysed and extracted. The organic phases are then dried over MgSO$_4$, filtered and concentrated under reduced pressure. Chromatography over silica gel (ethyl acetate/hexane:30/70) enables the expected product to be isolated.

Step C:2-Amino-3-bromopyridine

The compound obtained in Step B is refluxed for 3 hours in a 50% 12N HCl solution. The reaction mixture is then cooled and washed with ether. The aqueous phase is then rendered basic by the addition of potassium hydroxide solution and subsequently extracted with dichloromethane. The organic phases are then dried over magnesium sulphate, filtered and concentrated under reduced pressure, enabling the expected product to be obtained.

Preparation B

N-(3-Bromo-2-pyridyl)-N-methylamine 1 equivalent of the compound of Preparation A diluted in 60 ml of tetrahydrofuran is added at room temperature to a solution of 1.1 equivalents of sodium hydride in 60 ml of tetrahydrofuran. The reaction mixture is then heated at 40° C. for 30 minutes, and then 1 equivalent of methyl iodide is added at −30° C. The solution is then brought back to room temperature for 8 hours. The reaction mixture is subsequently poured into ice and then extracted with ether and with dichloromethane. The organic phases are then washed with water, dried over MgSO$_4$, filtered and evaporated under reduced pressure. Chromatography over silica gel (ethyl acetate/hexane) enables the expected product to be isolated.

Preparation C

N-(3-Bromo-2-pyridyl)-N-ethylamine

The procedure is as for Preparation B using ethyl iodide as reagent. The reagent is added at room temperature and then the reaction mixture is maintained at reflux of the tetrahydrofuran for 8 hours.

Preparation D

N-(3-Bromo-2-pyridyl)-N-propylamine

The procedure is as for Preparation B using 1-bromopropane as reagent.

Preparation E

N-(3-Bromo-2-pyridyl)-N-butylamine

The procedure is as for Preparation D using 1-bromobutane as reagent.

Preparation F

N1-(3-Bromo-2-pyridyl)-N2,N2-dimethyl-1,2-ethanediamine

The procedure is as for Preparation B using 2-chloro-N,N-dimethylethylamine hydrochloride as reagent. The reagent is added at 0° C. and once the addition is complete 1 equivalent of sodium hydride is added, and then the reaction mixture is subjected to reflux of the tetrahydrofuran for 48 hours.

Preparation G

N1-(3-Bromo-2-pyridyl)-N2,N2-dimethyl-1,3-propanediamine

The procedure is as for Preparation F using 3-chloro-N,N-dimethylpropylamine hydrochloride as reagent.

EXAMPLE 1

5,10-Dimethyl-5,10-dihydrodipyrido[2,3-b:2,3-e]pyrazine 2 equivalents of tert-butanol are added dropwise at room temperature to 7 equivalents of sodium amide in 10 ml of tetrahydrofuran (concentration=70 mM). The solution is heated for 2 hours at 45° C., and then cooled under a stream of nitrogen at 0° C. 1 equivalent of the compound obtained in Preparation B dissolved in 80 ml of tetrahydrofuran (concentration=30 mM) is then added to the reaction mixture. After 3 days' reaction at room temperature, the reaction mixture is poured into ice and then extracted with dichloromethane. The organic phase is then dried over magnesium sulphate, filtered and concentrated under reduced pressure. Chromatography over silica gel (hexane/acetone) enables the expected product to be isolated.

Melting point:152° C.

EXAMPLE 2

5,10-Dimethyl-5,10-dihydrodipyrido[2,3-b:3,2-e]pyrazine

The product is isolated during the purification of the compound obtained in Example 1.

Melting point:150° C.

EXAMPLE 3

5,10-Diethyl-5,10-dihydrodipyrido[2,3-b:2,3-e]pyrazine

The procedure is as for Example 1 using the compound obtained in Preparation C as substrate.

Melting point:145° C.

EXAMPLE 4

5,10-Diethyl-5,10-dihydrodipyrido[2,3-b:3,2-e]pyrazine

The product is isolated during the purification of the compound obtained in Example 3.

Melting point:131° C.

EXAMPLE 5

5,10-Dibutyl-5,10-dihydrodipyrido[2,3-b:2,3-e]pyrazine

The procedure is as for Example 1 using the compound obtained in Preparation E as substrate.

Melting point:94° C.

EXAMPLE 6

5,10-Dibutyl-5,10-dihydrodipyrido[2,3-b:3,2-e]pyrazine

The product is isolated during the purification of the compound obtained in Example 5.

Melting point:115° C.

EXAMPLE 7

N1,N1-Dimethyl-2-{50-[2-(dimethylamino)ethyl]-5,10-dihydrodipyrido[2,3-b:2,3-e]pyrazin-5-yl}-1-ethanamine The procedure is as for Example 1 using the compound obtained in Preparation F as substrate.

Melting point:144° C.

EXAMPLE 8

N1,N1-Dimethyl-3-{10-[3-(dimethylamino)propyl]-5,10-dihydrodipyrido[2,3-b:2,3-e]pyrazin-5-yl}-1-propanamine The procedure is as for Example 1 using the compound obtained in Preparation G as substrate.

Melting point:100° C.

EXAMPLE 9

N1,N1-Dimethyl-3-{10-[3-(dimethylamino)propyl]-5,10-dihydrodipyrido[2,3-b:3,2-e]pyrazin-5-yl}-1-propanamine The product is isolated during the purification of the compound obtained in Example 8.

Melting point:84° C.

EXAMPLE 10

5,10-Dipropyl-5,10-dihydrodipyrido-[2,3-b:2,3-e]pyrazine

The compound obtained in Example 1 is added to a solution, cooled to −10° C., containing 4 equivalents of n-butyllithium (1.6M in hexane), in 30 ml of tetrahydrofuran (concentration=8 mM). After 4 hours' reaction at 0° C., the reaction mixture is cooled to −30° C. and 4 equivalents of ethyl iodide are added rapidly. The reaction mixture is then brought to room temperature, and subsequently hydrolysed using a mixture of water/ice. After extraction with ether, the organic phases are dried over MgSO$_4$, filtered and concentrated under reduced pressure Chromatography over silica gel (hexane/ethyl acetate:90/10)enables the expected product to be isolated.

Melting point:126° C.

EXAMPLE 11

5-Methyl-10-propyl-5,10-dihydrodipyrido[2,3-b:2,3-e]pyrazine

The product is isolated during the purification of the compound obtained in Example 10.

EXAMPLE 12

5,10-Di-[(methylthio)methyl]-5,10-dihydrodipyrido [2,3-b:2,3-e]pyrazine 4 equivalents of tetramethylethylenediamine diluted in 20 ml of tetrahydrofuran (concentration=8 mM) are added, at −70° C., to a solution containing 4 equivalents of n-butyllithium (1.6M in hexane) in 30 ml of tetrahydrofuran (concentration=8 mM). The temperature is brought to −20° C. in the course of 1 hour, and then to −5° C., and the compound obtained in Example 1 is added to the reaction mixture. After 4 hours' reaction at 0° C., the mixture is cooled again to −30° C. and 4 equivalents of dimethyl disulphide are added. The reaction mixture is then brought to room temperature, and subsequently hydrolysed using a mixture of water/ice. After extraction with ether, the organic phases are dried over MgSO$_4$, filtered and concentrated under reduced pressure. Chromatography over silica gel (hexane/ethyl acetate:90/10) enables the desired product to be isolated.

Melting point:169° C.

EXAMPLE 13

5-Methyl-10-[(methylthio)methyl]-5,10-dihydrodipyrido-[2,3-b:2,3-e]pyrazine

The product is isolated during the purification of the compound obtained in Example 12.

Melting point:108° C.

EXAMPLE 14

5,10-Dimethyl-4-(methylthio)-5,10-dihydrodipyrido [2,3-b:2,3-e]pyrazine

The product is isolated during the purification of the compound obtained in Example 12.

Melting point:88° C.

EXAMPLE 15

5,10-Di-(2-methoxyethyl)-5,10-dihydrodipyrido[2,3-b:2,3-e]pyrazine

The procedure is as for Example 10, replacing ethyl iodide by chloro-(methoxy)-methane.

Melting point:108° C.

EXAMPLE 16

5,10-Dimethyl-4-(methylthio)-5,10-dihydrodipyrido [2,3-b:3,2-e]pyrazine

The procedure is as for Example 10, using the product obtained in Example 2 as substrate and using dimethyl disulphide as reagent.

Melting point:99° C.

EXAMPLE 17

4-Methoxymethyl-5,10-dimethyl-5,10-dihydrodipyrido[2,3-b:3,2-e]pyrazine

The procedure is as for Example 16, using as electrophilic reagent the reagent used in Example 15.

Melting point:95° C.

EXAMPLE 18

5,10-Dibutyl-4-(methylthio)-5,10-dihydrodipyrido[2,3-b:3,2-e]pyrazine

The procedure is as for Example 10 using the product obtained in Example 6 as substrate and using dimethyl disulphide as reagent.

EXAMPLE 19

5,10-Dimethyl-2-nitro-5,10-dihydrodipyrido[2,3-b:2,3-e]pyrazine

Oxalic acid is added at room temperature to a solution containing 1 equivalent of the compound obtained in Example 1 in 50 ml of dichloromethane (concentration=6 mM). After 20 hours' reaction, the reaction mixture is filtered and the precipitate is washed with dichloromethane and then dried under reduced pressure. The resulting product is added to 50 ml of nitromethane (concentration=6 mM), and then potassium nitrate is added in excess. After 48 hours' reaction at room temperature, the reaction mixture is poured into a 1 M potassium hydroxide solution. After extraction with dichloromethane, the combined organic phases are dried over sodium sulphate, filtered and concentrated under reduced pressure. Chromatography over silica gel (hexane/ethyl acetate:50/50) enables the expected product to be isolated.

Melting point:212° C.

EXAMPLE 20

5,10-Dibutyl-2-nitro-5,10-dihydrodipyrido[2,3-b:2,3-e]pyrazine

The procedure is as for Example 19, using the compound obtained in Example 5 as substrate.

Melting point: 111° C.

EXAMPLE 21

5,10-Dibutyl-2,7-dinitro-5,10-dihydrodipyrido[2,3-b:2,3-e]pyrazine

The product is isolated during the purification of the compound obtained in Example 20.

Melting point:221° C.

EXAMPLE 22

N1,N1-Dimethyl-2-{10-[2-(dimethylamino)ethyl]-2-nitro-5,10-dihydrodipyrido[2,3-b:2,3-e]pyrazin-5-yl}-1-ethylamine The procedure is as for Example 19, using the product obtained in Example 7 as substrate.

Melting point: 110° C.

EXAMPLE 23

N1,N1-Dimethyl-3-{10-[3-(dimethylamino)propyl]-2-nitro-5,10-dihydrodipyrido[2,3-b:2,3-e]pyrazin-5-yl}-1-propanamine The procedure is as for Example 19, using the product obtained in Example 8 as substrate.

Melting point: 95° C.

EXAMPLE 24

N1,N1-Dimethyl-3-{10-[3-(dimethylamino)propyl]-2,7-dinitro-5,10-dihydrodipyrido[2,3-b:2,3-e] pyrazin-5-yl}-1-propanamine The product is isolated during the purification of the compound obtained in Example 23.

EXAMPLE 25

5,10-Dimethyl-2-nitro-5,10-dihydrodipyrido[2,3-b:3,2-e]pyrazine

The procedure is as for Example 19 using the compound obtained in Example 2 as substrate.

EXAMPLE 26

5,10-Dimethyl-2,8-dinitro-5,10-dihydrodipyrido[2,3-b:3,2-e]pyrazine

The product is isolated during the purification of the compound obtained in Example 25.
Melting point: >270° C.

EXAMPLE 27

N1,N1-Dimethyl-3-{10-[3-(dimethylamino)propyl]-2-nitro-5,10-dihydrodipyrido[2,3-b:3,2-e]pyrazin-5-yl}-1-propanamine The procedure is as for Example 19, using the compound obtained in Example 9 as substrate.
Melting point: 123° C.

EXAMPLE 28

N1,N1-Dimethyl-3-{10-[3-(dimethylamino)propyl]-2,8-dinitro-5,10-dihydrodipyrido[2,3-b:3,2-e]pyrazin-5-yl}-1-propanamine The product is isolated during the purification of the compound obtained in Example 27.
Melting point: 160–170° C.

EXAMPLE 29

5,10-Dibutyl-2,8-dinitro-5,10-dihydrodipyrido[2,3-b:3,2-e]pyrazine

The procedure is as for Example 19 using the compound obtained in Example 6 as substrate.
Melting point: 202° C.

EXAMPLE 30

2-Amino-5,10-dimethyl-5,10-dihydrodipyrido[2,3-b:2,3-e]pyrazine

A solution containing 1 equivalent of the compound obtained in Example 19 in 50 ml of methanol (concentration=1 mM), 100 mg of 10% palladium-on-carbon and 4.6 equivalents of ammonium formate is heated for 3 hours at 40° C. After returning to room temperature, the reaction mixture is filtered over Celite, and then concentrated under reduced pressure, enabling the desired product to be isolated.
Melting point: 134° C.

EXAMPLE 31

N1,N1-Dimethyl-2-{10-[2-(dimethylamino)ethyl]-2-amino-5,10-dihydrodipyrido[2,3-b:2,3-e]pyrazin-5-yl}-1-ethylamine The procedure is as for Example 30 using the compound obtained in Example 22 as substrate.
Melting point: 139° C.

EXAMPLE 32

N1,N1-Dimethyl-3-{10-[3-(dimethylamino)propyl]-2-amino-5,10-dihydrodipyrido[2,3-b:2,3-e]pyrazin-5-yl}-1-propanamine The procedure is as for Example 30 using the compound obtained is Example 23 as substrate.
Melting point: 98° C.

EXAMPLE 33

2-Amino-5,10-dimethyl-5,10-dihydrodipyrido[2,3-b:3,2-e]pyrazine

The procedure is as for Example 30 using the compound obtained in Example 25 as substrate.
Melting point: 124° C.

EXAMPLE 34

N1,N1-Dimethyl-3-{10-[3-(dimethylamino)propyl]-2-amino-5,10-dihydrodipyrido[2,3-b:3,2-e]pyrazin-5-yl}-1-propanamine The procedure is as for Example 30 using the compound obtained in Example 27 as substrate.

EXAMPLE 35

N1-(5,10-Dimethyl-5,10-dihydrodipyrido[2,3-b:3,2-e]pyrazin-2-yl)-1-benzenesulphonamide 1.2 equivalents of benzenesulphonyl chloride diluted in 10 ml of dichloromethane (concentration=1 mM) are added dropwise to a solution, at −20° C., of 3 equivalents of pyridine in 25 ml of dichloromethane (concentration=3 mM). After 1 hour's reaction, 1 equivalent of the compound obtained in Example 33 is added, and the reaction mixture is then brought to room temperature. After 12 hours, the reaction mixture is hydrolysed, and then extracted with dichloromethane. The combined organic phases are dried over sodium sulphate, filtered and concentrated under reduced pressure. Chromatography over silica gel (hexane/ethyl acetate: 60/40) enables the expected product to be isolated.
Melting point: 208° C.

EXAMPLE 36

5,10-Dimethyl-5,10-dihydrodipyrido[2,3-b:2,3-e]pyrazine-2-carbaldehyde 10 equivalents of POCl$_3$ are added dropwise to 23 equivalents of dimethylformamide cooled to 0° C., and the reaction mixture is brought to room temperature. After 20 minutes, the solution is added dropwise to a solution of one equivalent of the compound obtained in Example 1 diluted in dichloro-1,2-ethane. The addition is effected with reflux of the dichloro-1,2-ethane, which is maintained for 20 hours. The reaction mixture is then cooled to 0° C., and then a 3 M potassium hydroxide solution (120 ml) is added and the mixture is heated to reflux. After 3 hours, the reaction mixture is cooled and extracted with dichloromethane. The combined organic phases are then washed with water, dried over magnesium sulphate, filtered and concentrated under reduced pressure. Chromatography over silica gel (hexane/ethyl acetate: 70/30) enables the expected product to be isolated.
Melting point: 176° C.

EXAMPLE 37

5,10-Dimethyl-5,10-dihydrodipyrido[2,3-b:2,3-e]pyrazine-2-carbaldehyde

The product is isolated during the purification of the compound obtained in Example 36.

EXAMPLE 38

5,10-Dimethyl-5,10-dihydrodipyrido[2,3-b:3,2-e]
pyrazine-3-carbaldehyde

The procedure is as for Example 36 using the compound obtained is Example 2 as substrate.

Melting point: 157° C.

EXAMPLE 39

N1-[5,10-Dimethyl-5,10-dihydrodipyrido[2,3-b:2,3-e]pyrazin-2-yl)methyl]-N2,N2-dimethyl -1,2-ethanediamine 3.6 equivalents of N,N-dimethylethylenediamine diluted in 25 ml of dichloromethane (concentration=6 mM) are added rapidly to a solution of 1 equivalent of the compound obtained in Example 36 in 25 ml of dichloromethane (concentration=2 mM). After one hour at room temperature, the solvent is removed by evaporation under reduced pressure and replaced by methanol. 10 equivalents of $NaBH_4$ are then added slowly to the reaction mixture. After 15 minutes' reaction, the mixture is poured into ice, and then extracted with dichloromethane. The organic phases are dried over magnesium sulphate, filtered and evaporated under reduced pressure. Chromatography over silica gel (triethylamine/methanol:50/50) enables the expected product to be isolated.

EXAMPLE 40

N1-[5,10-Dimethyl-5,10-dihydrodipyrido[2,3-b:3,2-e]pyrazin-2-yl)methyl]-N2,N2-dimethyl -1,2-ethanediamine The procedure is as for Example 39 using the compound obtained in Example 38 as substrate.

Melting point: oil.

EXAMPLE 41

2-Bromo-5,10-dibutyl-5,10-dihydrodipyrido[2,3-b:3,2-e]pyrazine 1.1 equivalents of phenyltrimethylammonium tribromide dissolved in 50 ml of tetrahydrofuran (concentration=2 mM) are added at room temperature to a solution of one equivalent of the compound obtained in Example 6 diluted in 50 ml of tetrahydrofuran (concentration=2 mM). After 24 hours' reaction, the reaction mixture is hydrolysed and then extracted with ether. The combined organic phases are dried over $MgSO_4$, filtered and concentrated under reduced pressure. Chromatography over silica gel (hexane/ethyl acetate:98/2) enables the expected product to be isolated.

EXAMPLE 42

2,8-Dibromo-5,10-dibutyl-5,10-dihydrodipyrido[2,3-b:3,2-e]pyrazine

The product is isolated during the purification of the compound obtained in Example 41.

Melting point: oil.

EXAMPLE 43

N1,N2-Di[5,10-dimethyl-5,10-dihydrodipyrido[2,3-b:3,2-e]pyrazin-2-yl)methyl]-1,2-ethanediamine One equivalent of 1,2-diaminoethane diluted in 25 ml of dichloromethane (concentration=2 mM) is added to a solution of two equivalents of the compound obtained in Example 38 diluted in 25 ml of dichloromethane (concentration=2 mM). After 30 minutes' reaction at room temperature, the solution is concentrated under reduced pressure and then the residue is diluted in 25 ml of methanol (concentration=2 mM). 10 equivalents of $NaBH_4$ are then added slowly, and after 30 minutes the reaction mixture is hydrolysed at 0° C. After extraction with dichloromethane, the combined organic phases are dried over magnesium sulphate, filtered and concentrated under reduced pressure. The residue is then eluted with methanol over silica gel. The fractions are evaporated under reduced pressure and then taken up in dichloromethane and evaporated again under reduced pressure, so enabling the expected product to be isolated.

Melting point: 171° C.

EXAMPLE 44

N1,N3-Di[5,10-dimethyl-5,10-dihydrodipyrido[2,3-b:3,2-e]pyrazin-2-yl)methyl]-1,3-propanediamine The procedure is as for Example 43, using 1,3-diaminopropane as reagent.

Melting point: 61° C.

EXAMPLE 45

N1,N2-Di[5,10-dimethyl-5,10-dihydrodipyrido[2,3-b:2,3-e]pyrazin-2-yl)methyl]-1,2-ethanediamine The procedure is as for Example 43, using the compound obtained in Example 37 as substrate.

Melting point: 80–90° C.

EXAMPLE 46

N1-[(E)-1-(5,10-Dimethyl-5,10-dihydrodipyrido[2,3-b:2,3-e]pyrazin-2-yl)methylidene]-N2-[(Z)-1-(5,10-dimethyl-5,10-dihydrodipyrido-[2,3-b:2,3-e]pyrazin-2-yl)methylidene]-1,2-ethanediamine The product is obtained during the synthesis of the compound of Example 45 when the reaction is stopped before the treatment with sodium borohydride.

EXAMPLE 47

N1-[(E)-1-(5,10-Dimethyl-5,10-dihydrodipyrido[2,3-b:3,2-e]pyrazin-2-yl)methylidene]-N3-[(Z)-1-(5,10-dimethyl-5,10-dihydrodipyrido-[2,3-b:3,2-e]pyrazin-2-yl)methylidene]-1,3-propanediamine The product is obtained during the synthesis of the compound of Example 44 when the reaction is stopped before the treatment with sodium borohydride.

EXAMPLE 48

N1-[(E)-1-(5,10-Dimethyl-5,10-dihydrodipyrido[2,3-b:3,2-e]pyrazin-2-yl)methylidene]-N2-[(Z)-1-(5,10-dimethyl-5,10-dihydrodipyrido[2,3-b:3,2-e]pyrazin-2-yl)methylidene]-1,2-ethanediamine The product is obtained during the synthesis of the compound of Example 43 when the reaction is stopped before the treatment with sodium borohydride.

EXAMPLE 49

N1,N4-Di[(5,10-dimethyl)-5,10-dihydrodipyrido[2,3-b:3,2-e]pyrazin-2-yl)methyl]-1,4-butanediamine The procedure is as for Example 43, using 1,4-diaminobutane as reagent.

EXAMPLE 50

N1-[(E)-1-(5,10-Dimethyl-5,10-dihydrodipyrido[2, 3-b:3,2-e]pyrazin-2-yl)methylidene]-N4-[(Z)-1-(5, 10-dimethyl-5,10-dihydrodipyrido-[2,3-b:3,2-e] pyrazin-2-yl)methylidene]-1,4-butanediamine The product is obtained during the synthesis of the compound of Example 49 when the reaction is stopped before the treatment with sodium borohydride.

EXAMPLE 51

5,10-Dibutyl-5,10-dihydrodipyrido[2,3-b:3,2-e] pyrazine-2-carbaldehyde

The procedure is as for Example 36 using the compound obtained in Example 6 as substrate.

Melting point: 108° C.

EXAMPLE 52

5,10-Dibutyl-5,10-dihydrodipyrido[2,3-b:2,3-e] pyrazine-2-carbaldehyde

The procedure is as for Example 36 using the compound obtained in Example 5 as substrate.

Melting point: 95° C.

EXAMPLE 53

5,10-Dibutyl-2-nitro-5,10-dihydrodipyrido[2,3-b:3, 2-e]pyrazine

The product is isolated during the purification of the compound obtained in Example 29.

Melting point: 128° C.

EXAMPLE 54

2-[10-(2-Hydroxy-2-phenylethyl)-5,10-dihydrodipyrido[2,3-b:2,3-e]pyrazin-5-yl]-1-phenyl-1-ethanol The procedure is as for Example 12 using benzaldehyde as reagent instead of dimethyl disulphide.

Melting point: 189° C.

EXAMPLE 55

(5,10-Dimethyl-5,10-dihydrodipyrido[2,3-b:3,2-e] pyrazin-4-yl)-(phenyl)methanol

The procedure is as for Example 54 using the compound of Example 2 as substrate.

Melting point: 126° C.

EXAMPLE 56

5,10-Dimethyl-5,10-dihydrodipyrido[2,3-b:3,2-e] pyrazin-4-carbaldehyde 0.47 mmol of the compound of Example 2 is added to a solution of 0.94 mmol of n-butyllithium (1.6 M in hexane) in 2 ml of tetrahydrofuran at −10° C. After one hour's reaction at −10° C., the temperature is lowered to −30° C. and 2 to 5 equivalents of dimethylformamide are added. The reaction mixture is then brought to room temperature, hydrolysed and then extracted with dichloromethane. After the organic phases have been dried, filtered and concentrated under reduced pressure, chromatography over silica gel (ethyl acetate/hexane:10/90) of the residue enables the expected product to be isolated.

Melting point: 184–185° C.

EXAMPLE 57

N1,N3-Di[(5,10-dimethyl-5,10-dihydrodipyrido[2,3-b:3,2-e]pyrazin-4-yl)methyl]-1,3-propanediamine The procedure is as for Example 43 using the compound of Example 56 as substrate and using 1,3-diaminopropane as reagent.

Mass spectrometry: (ionic spray): [M+1]: m/z=523.5

EXAMPLE 58

N1,N7-Di[(5,10-dimethyl-5,10-dihydrodipyrido[2,3-b:3,2-e]pyrazin-2-yl)methyl]-1,7-heptanediamine The procedure is as for Example 43 using the using 1,7-diaminoheptane as reagent.

Mass spectrometry: (ionic spray): [M+1]: m/z=551.5

EXAMPLE 59

N1-[(5,10-Dimethyl-5,10-dihydrodipyrido[2,3-b:3,2-e]pyrazin-2-yl)methyl]-N3-(3-{[5,10-dimethyl-5,10-dihydrodipyrido[2,3-b:3,2-e]-pyrazin-2-yl)methyl] amino}propyl-N3-methyl-1,3-propanediamine The procedure is as for Example 43 using N,N-bis(3-aminopropyl)-N-methylamine as reagent.

Mass spectrometry: (ionic spray): [M+1]: m/z=594.5

EXAMPLE 60

N1,N3-Di[(5,10-dimethyl-5,10-dihydrodipyrido[2,3-b:3,2-e]pyrazin-2-yl)-N1,N3-dimethyl]-1,3-propanediamine The procedure is as for Example 43 using the using N1,N3-dimethyl-1,3-propanediamine as reagent.

Mass spectrometry: (ionic spray): [M+1]: m/z=551.5

EXAMPLE 61

N-[(5,10-Dimethyl-5,10-dihydrodipyrido[2,3-b:3,2-e]pyrazin-2-yl)-methyl]-2-(2-{[5,10-dimethyl-5,10-dihydrodipyrido[2,3-b:3,2-e]-pyrazin-2-yl)methyl] amino}ethoxy)-1-ethanamine The procedure is as for Example 43 using 2-(2-aminoethoxy)-1-ethanamine as reagent.

EXAMPLE 62

5,10-Dimethyl-4-(trimethylsilyl)-5,10-dihydrodipyrido[2,3-b:3,2-e]pyrazine

The procedure is as for Example 56 using trimethylsilyl chloride as reagent on the place of dimethylformamide.

Mass spectrometry: (ionic spray): [M+1]: m/z=285

EXAMPLE 63

5,10-Dimethyl-4-(trimethyltin)-5,10-dihydrodipyrido [2,3-b:3,2-e]pyrazine

The procedure is as for Example 56 using trimethyltin chloride as reagent on the place of dimethylformamide.

Mass spectrometry: (ionic spray): [M+1, $Sn^{116}$]: m/z=373 [M+1, $Sn^{118}$]: m/z=375 [M+1, $Sn^{120}$]: m/z=377

EXAMPLE 64

(5,10-Dimethyl-5,10-dihydrodipyrido[2,3-b:3,2-e] pyrazin-4-yl)(diphenyl)methanol The procedure is as for Example 56 using benzophenone as reagent on the place of dimethylformamide.

Mass spectrometry: (ionic spray): [M+1]: m/z=395,5

EXAMPLE 65

5,10-Dimethyl-5,10-dihydrodipyrido-4-iodo[2,3-b:3, 2-e]pyrazine

The procedure is as for Example 56 using iodide as reagent.

Mass spectrometry: (ionic spray): [M+1]: m/z=339

EXAMPLE 66

Sodium 5,10-dimethyl-5,10-dihydrodipyrido[2,3-b:3,2-e]pyrazine-4-carboxylate 0.47 mmol of the compound of Example 2 is added to a solution of 0.94 mmol of n-butyllithium (1.6 M in hexane) in 2 ml of tetrahydrofuran at −10° C. After one hour's reaction at −10° C., the reaction mixture is put under $CO_2$ current during 20 minutes. The reaction mixture in then brought to room temperature, hydrolysed and then extracted with dichloromethane. A concentration under reduced pressure of the aqueous phase enables the expected product to be isolated.

EXAMPLE 67

Ethyl 5,10-dimethyl-5,10-dihydrodipyrido[2,3-b:3,2-e]pyrazine-4-carboxylate 0.47 mmol of the compound of Example 2 is added to a solution of 0.94 mmol of n-butyllithium (1.6 M in hexane) in 2 ml of tetrahydrofuran at −10° C. After one hour's reaction at −10° C., 2 to 5 equivalents of ethyl chloroformate are added. The reaction mixture in then brought to room temperature, hydrolysed and extracted with dichloromethane. After the organic phases have been dried, filtered and concentrated under reduced pressure, chromatography over silica gel (ethyl acetate/hexane:95/5) of the residue enables the expected product to be isolated.

Mass spectrometry: (ionic spray): [M+1]: m/z=285,5

EXAMPLE 68

5,10-Dimethyl-N-propyl-5,10-dihydrodipyrido[2,3-b:3,2-e]pyrazine-4-carboxamide 0.43 mmol of 1-ethyl-3-(3'-dimethylaminoproyl)-carbodiimide hydrochloride are added at 0° C. to a solution of 0.39 mmol of the compound of Example 66, 0.37 mmol of propylamine, 0.43 mmol of N-hydroxybenzotriazol dissolved into 4 ml of dimethylformamide, and 0.49 mmol of triethylamine. After 12 hours at room temperature, the reaction mixture is hydrolysed and then extracted with dichloromethane. The organic phases are washed with 5% aqueous solution of $NaHCO_3$, dried, filtered and then concentrated under reduced pressure. A chromatography over silica gel (ethyl acetate/hexane:95/5) of the residue enables the expected product to be isolated.

EXAMPLE 69

N-{2-[-2-{[(5,10-dimethyl-5,10-dihydrodipyrido[2, 3-b:3,2-e]pyrazin-4-carbonyl]amino}ethyl)(methyl) amino]ethyl}-5,10-dimethyl-5,10-dihydrodipyrido[2, 3-b:3,2-e]pyrazine-4-carboxamide The procedure is as for Example 68 using 2 equivalents of the compound of Example 2 for one equivalent of the amino compound, and using N,N-bis(2-aminoethyl)-N-methylamine on the place of propylamine.

Pharmacological Studies of the Compounds of the Invention

EXAMPLE 70

Cytotoxicity of the Compounds

Three cell lines were used:
a murine leukaemia, L1210,
a murine melanoma, B16,
a human pulmonary carcinoma, non-small cell, A549.

The cells are cultured in complete RPMI 1640 medium containing 10% foetal calf serum, 2 mM glutamine, 50 units/ml of penicillin, 50 μg/ml of streptomycin and 10 mM Hepes. The cells are distributed in microplates and exposed to the cytotoxic compounds. They are then incubated for 2 days (L1210) and for 4 days (A549, B16). The number of viable cells is then quantified by a colorimetric assay, the Microculture Tetrazolium Assay (Cancer Res., 1987, 47, 936–942). The results are expressed as $IC_{50}$ values, which is the cytotoxic concentration that inhibits proliferation of the treated cells by 50%.

The results obtained show that the compounds of the invention exhibit good general cytotoxicity on the three cell lines, with $IC_{50}$ values of lower than 10 μM.

EXAMPLE 71

In vivo Activity

* Anti-tumour activity of the compounds on the leukaemia P388

The line P388 (murine leukaemia) was supplied by the National Cancer Institute (Frederick, USA). The tumour cells ($10^6$ cells) were inoculated on day 0 into the peritoneal cavity of female BDF1 mice (Iffa-Credo, France) weighing from 18 to 20 g (groups of 6 animals). The compounds were administered on day 1 or on days 1, 5, 9 by the intraperitoneal or intravenous route.

The anti-tumour activity is expressed as a % of T/C:

%T/C=Median survival time of the treated animals/Median survival time of the control animals×100

By way of indication, the compound of Example 44 is active in respect of the leukaemia P388: according to the administration scheme, it results in a T/C of from 150 to 190% at from 25 to 50 mg/kg.

* Anti-tumour activity of the compounds on the melanoma B16

The line B16 (murine melanoma) was supplied by the National Cancer Institute (Frederick, USA). The tumour is maintained by successive subcutaneous implants of tumour fragments. On day 0, the tumours are ground and homogenised in 0.9% NaCl (1 g of tumour in 10 ml), and 0.5 ml of the homogenate is injected into the peritoneal cavity of each BDF1 mouse. The products were administered once daily for 9 days, (D1–9) by the intra-peritoneal route, to groups of 7 animals.

The anti-tumour activity is expressed as a % of T/C. The compound of Example 44 is active in respect of the melanoma B16: it results in a T/C of from 140 to 150% at from 1.56 to 12.5 mg/kg.

EXAMPLE 72

Pharmaceutical Composition

Tablets

Formulation for the preparation of 1000 tablets containing 50 mg of active ingredient
Compound of Example 44
  5 g
Lactose
  40 g
Magnesium stearate
  10 g
Wheat starch
  15 g
Maize starch
  15 g
Silica
  3 g
Hydroxypropyl cellulose
  5 g

What is claimed is:

1. A compound selected from those of formula (I):

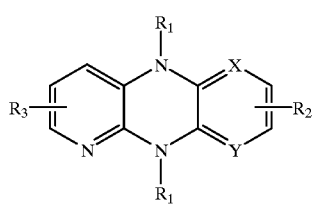

(I)

wherein:
X represents nitrogen, carbon or CH,
Y represents nitrogen, when X represents carbon, or CH, or Y represents carbon, or CH when X represents nitrogen it being understood that when X or Y represents carbon, then this carbon is substituted by $R_2$,
$R_1$ represents linear or branched ($C_1$–$C_6$)alkyl (optionally substituted by one or more, identical or different groups, selected from halogen, linear or branched ($C_1$–$C_6$)-alkylthio, linear or branched ($C_1$–$C_6$)alkoxy, monoalkyl- or dialkyl-amino wherein alkyl in each case is linear or branched and has 1 to 6 carbon atoms, aryl, hydroxy, formyl, linear or branched ($C_1$–$C_6$)alkoxycarbonyl, and carboxy), it being understood that the two $R_1$ have either identical definitions or different definitions,
$R_2$ and $R_3$, which may be identical or different, each independently of the other represents Z, or one of $R_2$ and $R_3$ represents W and the other of $R_2$ and $R_3$ represents Z in which
  Z represents:
    hydrogen,
    halogen
    linear or branched ($C_1$–$C_6$)alkyl, which alkyl may be substituted by one or more, identical or different groups, selected from hydroxy, linear or branched ($C_1$–$C_6$)alkoxy, aryl, amino (optionally substituted by one or two, identical or different groups, selected from linear or branched ($C_1$–$C_6$)alkyl, aryl, aryl-($C_1$–$C_6$)alkyl in which alkyl is linear or branched, aminoalkyl in which alkyl is linear or branched and has 1 to 6 carbon atoms monoalkylaminoalkyl in which each alkyl is linear or branched and has 1 to 6 carbon atoms dialkylaminoalkyl in which each alkyl is linear or branched and has 1 to 6 carbon atoms linear or branched ($C_1$–$C_6$)-hydroxyalkyl, and alkoxyalkyl in which each alkyl is linear or branched and has 1 to 6 carbon atoms, and formyl,
    amino (optionally substituted by one or two, identical or different groups, selected from linear or branched ($C_1$–$C_6$)alkyl, aryl, aryl-($C_1$–$C_6$)alkyl in which alkyl is linear or branched, linear or branched ($C_1$–$C_6$)-alkylsulphonyl, arylsulphonyl, aminoalkyl in which alkyl is linear or branched and has 1 to 6 carbon atoms monoalkylaminoalkyl in which each alkyl is linear or branched and has 1 to 6 atoms dialkylaminoalkyl in which each alkyl is linear or branched and has 1 to 6 atoms linear or branched ($C_1$–$C_6$)-hydroxyalkyl, and alkoxyalkyl in which each alkyl is linear or branched and has 1 to 6 carbon atoms),
    nitro,
    linear or branched ($C_1$–$C_6$)alkylthio,
    formyl,
    hydroxycarbonyl,
    linear or branched ($C_1$–$C_6$)alkoxycarbonyl,
    aminocarbonyl, monoalkylaminocarbonyl in which alkyl is linear or branched and has 1 to 6 carbon atoms, or dialkylaminocarbonyl in which each alkyl is linear or branched and has 1 to 6 carbon atoms,
  W represents linear or branched ($C_5$–$C_{24}$)alkylene, in which one to four carbon atoms are optionally replaced by one to four, identical or different groups, each independently of the other selected from oxygen, imine, —N($R_4$)—CO—, —CO—N($R_4$)—, and N($R_4$) wherein $R_4$ represents hydrogen or linear branched ($C_1$–$C_6$)alkyl, which alkylene is substituted in its terminal position by one of the following groups:

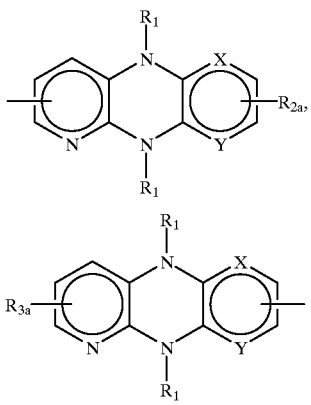

wherein X, Y and $R_1$ are as defined above, and $R_{2a}$, and $R_{3a}$ represent Z as defined above,
their isomers and pharmaceutically-acceptable acid or base addition salts thereof.

2. A compound of claim 1, wherein $R_2$ and $R_3$, which may be identical or different, each independently of the other represents Z, their isomers and pharmaceutically-acceptable acid or base addition salts thereof.

3. A compound of claim 1, wherein one $R_2$ and $R_3$ represents Z and the other of $R_2$ and $R_3$ represents W, their isomers and pharmaceutically-acceptable acid or base addition salts thereof.

4. A compound of claim 1, wherein one of $R_2$ and $R_3$ represents Z and the other of $R_2$ and $R_3$ represents $W_1$, which $W_1$ represents linear ($C_6$–$C_{12}$)alkylene in which two or three carbon are replaced by two or three, identical or different, $N(R_4)$ groups wherein $R_4$ represents hydrogen or linear or branched ($C_1$–$C_6$)alkyl, which alkylene is substituted in its terminal position by one of the following two groups:

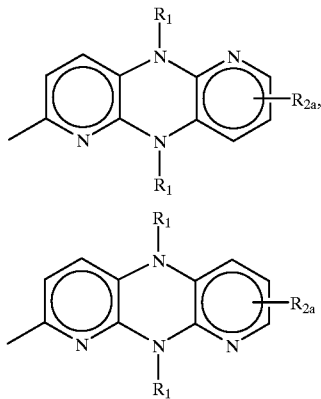

wherein $R_1$ is as defined in claim 1 and $R_{2a}$, represents Z, their isomers and pharmaceutically-acceptable acid or base addition salts thereof.

5. A compound of claim 1, wherein one of $R_2$ and $R_3$ represents Z and the other of $R_2$ and $R_3$ represents $W_2$ with a formula:

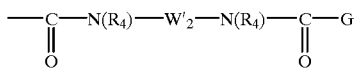

wherein:
$R_4$, which may be identical or different, represents hydrogen or linear or branched ($C_1$–$C_6$) alkyl,
$W'_2$ represents linear ($C_3$–$C_{12}$)-alkylene in which one, two carbon atoms are optionally replaced by one or two identical or different, $N(R_4)$ groups wherein $R_4$ is as defined above,
G represents one of the following groups:

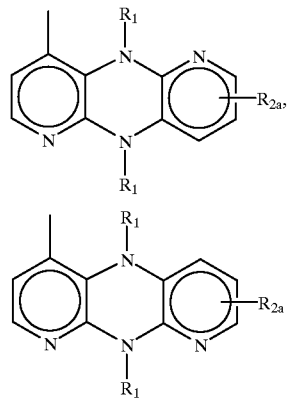

wherein $R_1$ is as defined in claim 1 and $R_{2a}$ represents Z, their isomers and pharmaceutically-acceptable acid or base addition salts thereof.

6. A compound of claim 4, wherein:
one of $R_2$ and $R_3$ represents $W_1$ wherein $R_1$ groups represent linear or branched ($C_1$–$C_6$) alkyl and $R_{2a}$ represents hydrogen, and the other of $R_2$ and $R_3$ represents Z corresponding to hydrogen, their isomers and pharmaceutically-acceptable acid or base addition salts thereof.

7. A compound of claim 5, wherein:
one of $R_2$ and $R_3$ represents $W_2$ wherein $R_1$ represent linear or branched ($C_1$–$C_6$) alkyl and $R_{2a}$ represents hydrogen,
and the other of $R_2$ and $R_3$ represents Z corresponding to hydrogen, their isomers and pharmaceutically-acceptable acid or base addition salts thereof.

8. A compound of claim 1, wherein $R_1$ represents linear or branched ($C_1$–$C_6$)alkyl, their isomers and pharmaceutically-acceptable acid or base addition salts thereof.

9. A compound of claim 1 which is selected from N1,N2-di[(5,10-dimethyl-5,10-dihydrodipyrido [2,3-b: 3,2-e] pyrazin-2-yl)methyl]-1,2-ethanediamine, its isomers and pharmaceutically-acceptable acid or base addition salts thereof.

10. A compound of claim 1 which is selected from N1,N3-di[(5,10-dimethyl-5,10-dihydrodipyrido [2,3-b: 3,2-e]pyrazin-2-yl)methyl]-1,3-propanediamine, its isomers and pharmaceutically-acceptable acid or base addition salts thereof.

11. A compound of claim 1 which is selected from N1,N4-di[(5,10-dimethyl-5,10-dihydrodipyrido [2,3-b: 3,2-e]pyrazin-2-yl)methyl]-1,4-butanediamine, its isomers and pharmaceutically-acceptable acid or base addition salts thereof.

12. A compound of claim 1 which is selected from N1-[(5,10-dimethyl-5,10-dihydrodipyrido-[2,3-b: 3,2-e]pyrazin-2-yl)methyl]-N3-(3-{[(5,10-dimethyl-5,10-dihydro-dipyrido-[2,3-b: 3,2-e]pyrazin-2-yl) methyl]amino}propyl)-N3-methyl-1,3-propanediamine, its isomers and pharmaceutically-acceptable acid or base addition salts thereof.

13. A compound of claim 1 which is selected from N1,N7-di[(5,10-dimethyl-5,10-dihydrodipyrido[2,3-b: 3,2-e]pyrazin-2-yl)methyl]-1,7-heptanediamine, its isomers and pharmaceutically-acceptable acid or base addition salts thereof.

14. A compound selected from those of formulae (α), (β), and (χ):

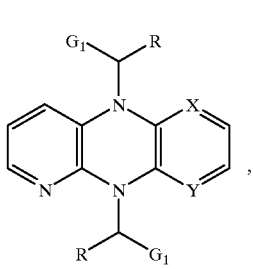

(α)

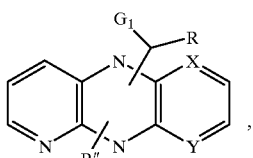

(β)

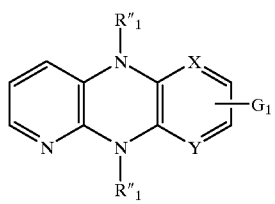

(X)

wherein:

X and Y are as defined for formula (I) in claim 1
$R''_1$ represents linear $(C_1-C_6)$alkyl,
R represents hydrogen or linear $(C_1-C_5)$alkyl,
$G_1$ represents tin, boron or silicon, each of those atoms being substituted by one or more linear or branched $(C_1-C_6)$alkyl, useful as intermediates in the synthesis of the compounds of formula (I).

15. A method for treating a living body afflicted with a cancer selected from the group consisting of carcinoma, leukaemia, melanoma, and neuroblastoma, comprising the step of administering to the living body an amount of a compound of claim 1, which is effective for alleviation of said cancer.

16. A pharmaceutical composition useful in treating cancer comprising as active principle an effective amount of a compound as claimed in claim 1, together with one or more pharmaceutically-acceptable excipients or vehicles.

* * * * *

UNITED STATES PATENT AND TRADEMARK OFFICE
CERTIFICATE OF CORRECTION

PATENT NO. : 6,127,369
DATED : October 3, 2000
INVENTOR(S) : Paul Caubere, et al.

It is certified that error appears in the above-identified patent and that said Letters Patent is hereby corrected as shown below:

Column 1,
Line 12, "make then" should read -- make them -- .

Column 3,
Line 11, "dihydronapththyl, " should read, -- dihydronaphthyl --.
Line 16, "-$C_1$-$C_6$)" should read -- ($C_1$-$C_6$) --.

Column 4,
Line 54, (approx.): "b:3,2-]" at the beginning of the line, should read: b: 3, 2e-] --.
Line 8, at the end of the line, "-N1 -" should begin a new line.

Column 16,
Line 19, "{50-" should read: -- {10- --.

Column 21,
Line 4, "pyrazine-3-carbaldehyde" should read: -- pyrazine-2-carbaldehyde --.

Column 24,
Line 19, "the using" at the end of the line should be deleted.
Line 39, "the using" at the end of the line should be deleted.

Column 26
Line 4, "-4-carbonyl]" should read: -- -4-yl) - carbonyl] --.

Column 28,
Line 17, insert "carbon" after the 6 and before "atoms".
Line 19, insert "carbon" after the 6 and before "atoms".

UNITED STATES PATENT AND TRADEMARK OFFICE
CERTIFICATE OF CORRECTION

PATENT NO.   : 6,127,369
DATED        : October 3, 2000
INVENTOR(S)  : Paul Caubere, et al.

It is certified that error appears in the above-identified patent and that said Letters Patent is hereby corrected as shown below:

Column 28,
Line 36, insert the word -- or -- after "or linear".

Column 29,
Line 39, At the end of the line, insert -- or -- after "one" and before the "comma".
Preliminary Amendment, Claim 5, line 7.

Signed and Sealed this

Twenty-third Day of October, 2001

Attest:

*Nicholas P. Godici*

NICHOLAS P. GODICI
*Attesting Officer*   *Acting Director of the United States Patent and Trademark Office*